United States Patent [19]

Häkkinen

[11] Patent Number: 4,638,812
[45] Date of Patent: Jan. 27, 1987

[54] EXHALATION FLOW METER

[75] Inventor: Taisto Häkkinen, Hämeenlinna, Finland

[73] Assignee: Etela Hameen Keuhkovammyhdistys R.Y., Finland

[21] Appl. No.: 637,211
[22] PCT Filed: Jan. 4, 1984
[86] PCT No.: PCT/FI83/00001
§ 371 Date: Jul. 19, 1984
§ 102(e) Date: Jul. 19, 1984
[87] PCT Pub. No.: WO84/02642
PCT Pub. Date: Jul. 19, 1984

[51] Int. Cl.[4] .............................................. A61B 5/08
[52] U.S. Cl. ................................... 128/726; 128/725; 272/99; 73/861.76
[58] Field of Search ................. 128/726, 725; 374/111; 73/861.74, 861.75, 861.76

[56] References Cited

U.S. PATENT DOCUMENTS

| 302,908 | 8/1884 | Haight | 374/111 |
|---|---|---|---|
| 966,050 | 8/1910 | Ramage | 128/726 |
| 2,296,973 | 9/1942 | Ardelt | 73/861.76 |
| 2,889,707 | 6/1959 | Snider | 73/861.75 |
| 3,564,419 | 7/1968 | Cronin et al. | 73/228 |
| 3,797,480 | 3/1974 | Williams | 128/2.08 |
| 3,826,247 | 7/1974 | Ruskin et al. | 279/99 X |
| 3,877,303 | 4/1975 | Beckman | 73/861.75 |
| 3,949,737 | 4/1976 | Nielsen | 128/726 |
| 4,041,935 | 8/1977 | Garbe | 279/99 X |
| 4,144,883 | 3/1979 | Grieshaber | 128/726 |
| 4,344,331 | 8/1982 | Iwasaki | 73/861.76 |

Primary Examiner—Kyle L. Howell
Assistant Examiner—John C. Hanley
Attorney, Agent, or Firm—Steinberg & Raskin

[57] ABSTRACT

The present invention concerns a device for measuring the peak flow of a person's exhalation. The device comprises a frame structure which is provided with a mouth piece. Inside the frame structure, a flap is disposed, along with a pointer. A spring of the flap has been disposed in a hollow space in the lower part of the flap, where the spring is not in contact with the exhaled air. The frame structure comprises a frame part and a transparent cover part, whereby the hygienic conditions of the interior of the device can be observed, without any need to open the same.

8 Claims, 7 Drawing Figures

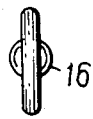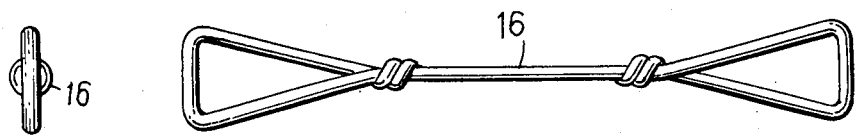
FIG. 4a
FIG. 4b
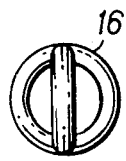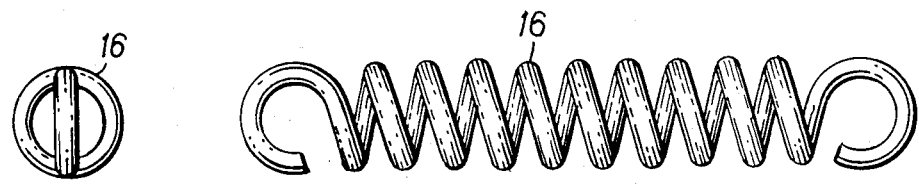
FIG. 5a
FIG. 5b

EXHALATION FLOW METER

BACKGROUND OF THE INVENTION

The present invention concerns a means intended for measuring the peak flow of a person's exhalation, said means comprising a frame structure provided with a mouthpiece part, a flap means accomodated within the frame structure, and a pointer means.

A means of this kind is termed a peak flow meter. The means is applicable in hospital as well as home use.

Regarding the state of art, reference is made to means in current use, such as e.g. "Mini-Wright" and "Vitalograph". A drawback of these means of prior art is their complex structure, in addition to which the hygienic condition of the means cannot be controlled without having to open the means.

SUMMARY OF THE INVENTION

The object of the present invention is to provide an improvement of similar means known in the art. The detailed object of the invention is to provide a means which in structure is remarkably simpler. A further object of the invention is to provide a means which is highly reliable as to its operation. Yet another object of the invention is to provide a means enabling the hygienic condition of the means' interior to be observed without need to open the means.

The aims of the invention are achieved by a means which is mainly characterized in that the spring means of the flap means has been placed in a hollow space in the lower part of the flap means, where the spring means is not in contact with the exhaled air.

By the means of the invention, numerous remarkable advantages are gained. The means of the invention is in its structure and size comparatively simpler and smaller than equivalent means known in the art. In the means of the invention, the spring design enables the reliability of the meter to be ascertained, after it has been used an investigated number of times, in that the user himself-/herself replaces the spring of the flap means, which can be done without any tools. In the design of the invention, the spring means of the flap means also is not in contact with the exhaled air. In the means of the invention, it is advantageous to use a transparent cover part, which enables the hygienic condition of the interior of the means to be observed without having to open the means.

BRIEF DESCRIPTION OF THE DRAWINGS

The invention is described in detail referring to an advantageous embodiment of the invention presented in the figures of the drawing attached, but to which the invention is not meant to be exclusively confined.

FIG. 4(a) is a view of spring means in accordance with the present invention;

FIG. 4(b) is a side view of FIG. 4(a);

FIG. 5(a) is a view similar to FIG. 4(a) of alternative spring means in accordance with the present invention; and FIG. 5(b) is a side view of FIG. 5(a).

Figure 2:
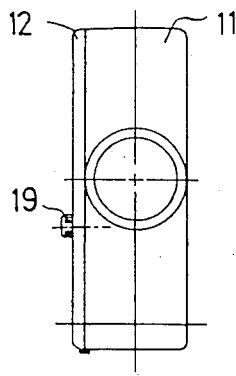
FIG. 2 is a right side elevational view of the embodiment of FIG. 1.
Figure 1:
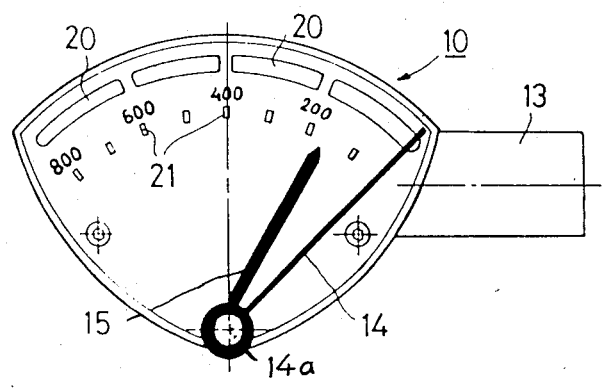
FIG. 1 is a front elevational view of one embodiment of the present invention.
Figure 3:
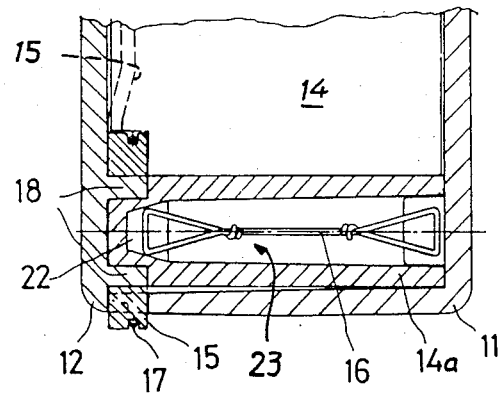
FIG. 3 is a view, partially in section, illustrating attachment of flap means and pointer means to a frame in accordance with the present invention.

In the embodiment depicted in FIGS. 1 to 3, the means of the invention in general has been indicated with the reference numeral 10. The means 10 comprises a frame structure, to which belongs a frame part 11 with a fixed mouthpiece part 13, and a cover part 12. If desired, it is also possible to attach to the fixed mouthpiece part 13 detachably a disposable mouthpiece part (not depicted). In the frame part 11 are provided tunnels for the fixing screws 19 of the cover part 12 and the mounting axle 18 for one end 14a of the flap means 14, this axle having a slot 22 for fixing one end of the spring means 16 to the flap means 14. The frame part 11 is also provided with suitably dimensioned flow apertures 20 for permitting unobstructed movement of the flap means 14.

The cover part 12 carries a graduation 21. The cover part 12 has holes for the fixing screws 19 of the cover part 12 and the mounting axle 18 for the pointer means 15, this axle being provided with the depression 22 for fixing one end 14a of the flap means 14. The cover part 12, too, has flow apertures 20 for achieving uniform movement of the flap means 14.

The flap means 14 has been arranged by the force of blowing to shift the pointer means 15. The lower part 14a of the flap means 14, attaching to the cover part 12, carries on one end a taper which seats in the fixing depression 22 in the cover part 12. The lower part 14a of the flap means 14 is hollow, this hollow space being indicated by the reference numeral 23. The spring means 16 are disposed in the hollow space 23 of the lower part 14a of the flap means 14. The spring means 16 has been arranged to cause in the flap means 14, while blowing is going on, a resistance that has been found to be appropriate and to return the flap means 14 to zero position when the flow has stopped. It is easy for the user himself/herself to remove the spring means 16 and, equally, to install it in place. The spring means 16 may be either a flat, bar or spiral spring (FIGS. 5(a) and 5(b)).

The pointer means 15 attaches to the mounting axle 18 on the cover part 12 by a compression spring 17. The compression spring 17 secures the pointer means 15 to the pointer means mounting axle 18 in the cover part 12. The cover part 12 is attached to the frame part 11 advantageously by fixing screws 19 provided with hexagonal nuts.

The cover part 12 has a graduated scale 21, laid out e.g. for 0–800 liters per minute. The scale may, of course, equally be laid out to display the reading in liters per second.

An exchangeable mouthpiece part may be attached to the mouthpiece part 13 on the frame part 11 when one means 10 is used by more than one person.

The operation of the means 10 of the invention is as follows. The person blows with maximum strength into the mouthpiece part 13, whereby the flap means 14 turnably mounted by its lower part 14a in the frame part 11 and in the cover part 12 is caused to turn forward, pushing the pointer means 15 ahead. After the pushing force caused by blowing has ceased, the flap means 14 returns, due to the spring force of the spring means 16, to its original position, and the pointer means 15 remains in place by effect of the friction caused by the compression spring 17 between the flap means 14 and the mounting axle 18 of the pointer means 15 in the cover part 12. The wedge-shaped point of the pointer means 15 points to the scale reading 21 printer on the cover part 12, equalling the person's exhaling capacity in liters per minute or liters per second.

In the foregoing, only one advantageous embodiment of the invention has been presented, and it its obvious to a person skilled in the art that numerous modifications thereof may be made within the scope of the inventive idea presented in the claims attached.

I claim:

1. A device for measuring peak flow of exhalation of an individual, said device comprising,
   a housing having an interior,
   an axle affixed to said housing in the interior thereof,
   a flap disposed within said housing interior and having a substantially tubular portion rotatably mounted on said axle,
   a spring mounted within said tubular portion, said spring having a first end connected to said tubular portion and a second end connected to said housing,
   a pointer rotatably mounted in said housing situated in a position to be contacted by said flap, and
   mouthpiece means provided on said housing for directing a flow of fluid into said housing interior, said flap and said pointer being situated in said housing with said flap being positioned between said pointer and said mouthpiece means,
   whereby upon initiating a flow of fluid through said mouthpiece means and into said housing interior, said flap rotates about said axle from an initial position and contacts and rotates said pointer to a position indicative of peak flow, and
   upon termination of said fluid flow, said spring returns said flap to the initial position, while said pointer remains at the position indicative of peak flow.

2. The device of claim 1, wherein said housing comprises a frame component and a transparent cover component.

3. The device of claim 2 additionally comprising a scale disposed upon said cover component.

4. The device of claim 2, additionally comprising
   at least one flow aperture disposed in said cover component.

5. The device of claim 1, wherein said spring is a torsion spring.

6. The device of claim 1, wherein said spring is a spiral spring.

7. The device of claim 1, wherein said pointer is rotatably mounted upon said axle.

8. The device of claim 7, additionally comprising
   a second spring, said second spring being a compression spring and being situated to compress said pointer on said axle,
   whereby said pointer remains at the position indicative of peak fluid flow.

* * * * *